(12) United States Patent
Haaslahti et al.

(10) Patent No.: US 7,826,052 B2
(45) Date of Patent: Nov. 2, 2010

(54) CORRECTION METHOD AND MEASUREMENT DEVICE FOR ANTI-STOKES PHOTOLUMINESCENCE MEASUREMENT

(75) Inventors: Ville Haaslahti, Turku (FI); Juhani Aalto, Turku (FI); Timo Oikari, Turku (FI); Tero Soukka, Turku (FI)

(73) Assignee: Hidex Oy, Turku (FI)

( * ) Notice: Subject to any disclaimer, the term of this patent is extended or adjusted under 35 U.S.C. 154(b) by 322 days.

(21) Appl. No.: 11/915,316

(22) PCT Filed: May 24, 2006

(86) PCT No.: PCT/FI2006/000164

§ 371 (c)(1),
(2), (4) Date: Jan. 24, 2008

(87) PCT Pub. No.: WO2006/125855

PCT Pub. Date: Nov. 30, 2006

(65) Prior Publication Data

US 2008/0174766 A1    Jul. 24, 2008

Related U.S. Application Data

(60) Provisional application No. 60/683,800, filed on May 24, 2005.

(30) Foreign Application Priority Data

May 24, 2005    (FI) .................................. 20050551

(51) Int. Cl.
G01N 21/64    (2006.01)

(52) U.S. Cl. ...................... 356/317; 356/307; 356/318; 356/417

(58) Field of Classification Search ................. 356/317, 356/318, 417

See application file for complete search history.

(56) References Cited

U.S. PATENT DOCUMENTS

2004/0076948 A1    4/2004    Petterson ........................ 435/5
2004/0076979 A1    4/2004    Belik et al. .................... 435/6

FOREIGN PATENT DOCUMENTS

| WO | WO 98/15830 | 4/1998 |
|----|-------------|--------|
| WO | WO 99/12018 | 3/1999 |
| WO | WO 2005/033709 | 4/2005 |

*Primary Examiner*—F. L Evans
(74) *Attorney, Agent, or Firm*—James C. Lydon

(57) ABSTRACT

A method to correct measurement error in a resonance energy-transfer assay, including exciting anti-Stokes photoluminescent donors with at least one wavelength of light which is greater than an emission wavelength of acceptor molecules; measuring emission at the acceptor's emission wavelength and which differs from the donor's emission wavelength in at least two different time windows; a first time window within the time window defined by the excitation light pulse and a second non-overlapping time window which follows the first time window; and correcting the emission signal, which includes signals originating from non-radiative and radiative energy transfer, within the first time window by estimating the ratio of the signals from non-radiative and radiative energy transfer or the signal originating from radiative energy transfer using at least one emission signal measured in the second time window.

9 Claims, 4 Drawing Sheets

CORRECTION METHOD AND MEASUREMENT DEVICE FOR ANTI-STOKES PHOTOLUMINESCENCE MEASUREMENT

This application is the National Stage of International Application No. PCT/FI2006/000164, filed May 24, 2006, which claims the benefit of U.S. provisional application Ser. No. 60/683,800, filed May 24, 2005, and foreign priority of Finnish application Ser. No. 20050551, filed May 24, 2005.

FIELD OF THE INVENTION

This invention relates to a method to correct for error in an anti-Stokes photoluminescence measurement and to a device employing the method. This invention relates particularly to a method to correct for radiant energy transfer component in a Foerster-type resonance energy transfer FRET-assay.

BACKGROUND OF THE INVENTION

The publications and other materials used herein to illuminate the background of the invention, and in particular, cases to provide additional details respecting the practice, are incorporated by reference.

Photoluminescence and Fluorescence Phenomenon

In traditional fluorescence phenomenon, such as photoluminescence a fluorescent molecule or ion is excited with light. Photons are absorbed by the target molecule or ion and the energy excites the target molecules or ions electrons to a higher energy state. When the excited energy state of the electrons is released, energy is released as a photon emitted by the molecule or ion. Characteristic for this phenomenon is that the energy of photons of the excitation radiation must be greater that of photons of the emission radiation, because part of the absorbed energy is lost in non-radiative processes within molecule or ion. This means that the excitation wavelength needs to be lower than the emission wavelength. This difference between excitation and emission wavelengths is called Stokes-shift.

Traditional fluorescence phenomenon has widely been used in the study of biomolecular interactions. Traditional fluorescence, however, has several limitations regarding use and sensitivity. In practice, because the fluorescence phenomenon is relatively common, the fluorescence originating from sample impurities, sample containers and components of the measurement equipment is a problem in bioassays. This kind of fluorescence is called autofluorescence.

Another problem with traditional fluorescence is small Stokes shift, meaning that excitation and emission wavelengths of the fluorescent compound are close to each other. This makes it difficult to select and limit the measured wavelength range of measurement instruments. The use of fluorescence and the problems related to its use in different bioassays have been described by Soini and Hemmilä, Clin Chem. (1979) 25:353-361, Fluoroimmunoassay: present status and key problems, and Hemmilä, Clin Chem. (1985) 31:359-370, Fluoroimmunoassays and immunofluorometric assays.

The problem of autofluorescence has been tried to be solved by using temporal resolution in fluorescence measurement. Technology called time-resolved fluorometry has been widely described by Soini and Lövgren, CRC Crit Rev Anal Chem (1987) 18: 105-154, Time-resolved fluorescence of lanthanide probes and applications in biotechnology. In time-resolved fluorescence the fluorescent markers are rare-earth metal ions i.e. lanthanide ions or organometallic compounds containing lanthanide ions such as lanthanide chelates or lanthanide cryptates. Lanthanide cryptates have been described in U.S. Pat. No. 6,352,672, Mabile et. al. ja Mathis G, Clin Chem (1993) 39: 1953-1959, Rare earth cryptates and homogeneous fluoroimmunoassays with human sera. Lanthanide chelates have been described by Hemmilä and Mukkala, Crt Rev Clin Lab Sci (2001) Time-resolution in fluorometry technologies, labels and applications in bioanalytical assays. Lanthanide chelate-dyed nanoparticles have been described by Härmä, Soukka and Lövgren, Clin Chem (2001) 47:561-568, Europium nanoparticles and time-resolved fluorescence for ultrasensitive detection of prostate specific antigen, and inorganic lanthanide particles by Beverloo, van Schadewijk, Zijlmans and Tanke, Anal Biochem (1992) 203: 326-334, Immunochemical detection of proteins and nucleic acids on filters using small luminescent inorganic crystals as markers. A time-resolved fluorometer for the measurement of longlifetime photo-luminescence of lanthanides has been described in Clin Chem. (1983) 29:65-68, Time-resolved fluorometer for lanthanide chelates—a new generation of nonisotopic immunoassays, by Soini and Kojola.

The lanthanides have a special characteristic feature of long lifetime of fluorescence. This means that if lanthanides are excited with a short duration light pulse with duration of e.g. 1 µs, the fluorescence emission of lanthanides continues for a long duration e.g. 500 µs-1 ms. Generally the autofluorescence originating from sample impurities, sample containers and components of measurement instrument lasts only about 10 ns. When the fluorescent emission is measured after the excitation light pulse has been turned off, e.g. the measurement is started after a 400 µs delay after the excitation light pulse, the background signal caused by autofluorescence has disappeared. This means that the lowest detectable concentration of the target molecule can be very low.

Another benefit of the time-resolved fluorescence is the large Stokes-shift characteristic to lanthanides. For example europium chelates and cryptates have excitation maximum at approximately 340 nm and emission maximum at approximately 616 nm.

Also time-resolved fluorescence has problems. Because lanthanides need high-energy photons (short wavelength) for excitation, the required excitation light source is complex and expensive. Suitable excitation light sources are e.g. Xenon flash lamp and a nitrogen laser. Another problem is that to reduce the long-lifetime autofluorescence and to be transparent to the ultraviolet excitation radiation, the employed optical components of the measurement instrument need to be of very high quality, e.g. all lenses must be pure quartz. A further problem both in traditional and time-resolved fluorescence is the operated wavelength range. Excitation light is in ultraviolet or visible range of the electromagnetic spectra. Absorption of especially ultraviolet light is high in biological sample matrixes. In addition, sample impurities often absorb light at visible range.

A solution for the described problems of traditional fluorescence and time-resolved fluorescence has been presented by Zarling et. al, WO 94/07142. The publication describes the so-called anti-Stokes photoluminescence method. In anti-Stokes photoluminescence the fluorescent marker is a crystal or a molecular structure constructed typically of two different lanthanide ions. These structures have a characteristic feature of being able to absorb two or three low energy photons of higher wavelength at 980 nm to excite one electron to a higher energy-state than the energy of any of the individual photons. As a result the electron is typically excited to a two or three times higher energy state than in traditional fluorescence or time-resolved fluorescence. Relaxation of the excited state can result in emission of one, two or three different principal wavelengths. A key feature is that the emission light is at a lower wavelength than the excitation light. This phenomenon able to produce so called anti-Stokes emission is called up-conversion. It eliminates the autofluorescence problem completely. Different inorganic upconverting phosphor compounds which produce anti-Stokes photoluminescence have been described by Wright, Mufti, Tagg, Webb and Schneider, Proc SPIE—Int Soc Opt Eng (1997) 2985: 248-255, High-sensitivity immunoassay using a novel upconverting phosphor reporter, Zijlmans, Bonnet, Burton, Kardos, Vail, Niedbala and Tanke, Anal Chem (1999), 267:30-36, Detection of cell and tissue surface antigens using up-converting phosphors: a new reporter technology, and U.S. Pat. No. 5,891,656, Zarling, Rossi, Peppers, Kane, Faris, Dyer, Ng and Schneider. Methods for excitation of up-converting photoluminescent phosphors using e.g. laser diode excitation at specified wavelength or broad spectrum light source and suitable excitation filter are described by Soukka et al. in WO 2004/086049 and Zarling et al. in U.S. Pat. No. 5,736,410.

Bioassays

The fluorescent labels and fluorescence measurement method described earlier are employed in so called bioassays, which are heterogeneous or homogeneous, requiring separation or separation free, respectively, bioaffinity binding assays or assays for biological effect e.g. enzymatic activity. Bioassays are used to study interaction of biomolecules, e.g. binding of antibodies to target antigen, or progress of enzymatic reaction, e.g. conversion of substrate to product. These kinds of assays are widely described by Price and Newman (eds.), Principles and practice of immunoassay, 1997; Macmillan, London, as well as US 2004/0076948, Pettersson.

Heterogeneous and Separation-based Assays

Traditional bioassays are heterogeneous i.e. separation based assays. In these assays a binder molecule, which is capable to recognize and bind a target molecule present in the sample, is immobilized onto a reaction vessel or another solid-phase. In competitive binding assays, another labelled molecule, which contains a fluorescent compound and able to bind to a molecule immobilized onto a reaction vessel is added to compete with the target molecule present in the sample. The target molecule present in the sample and the labelled molecule containing the fluorescent compound compete in binding to the binding sites of the immobilized molecules on the reaction vessel. After incubation (time for binding reaction to proceed) the reaction vessel is washed to remove both the unbound target molecules and labelled molecules from the vessel. Thereafter, the fluorescence produced by the bound labelled molecules is measured from the reaction vessel. When the sample contains a low concentration of target molecule, the fluorescence signal is high, because the labelled molecules have bound to the immobilized molecules. In case the concentration of target molecules in the sample is high, the binding sites of the immobilized molecules are occupied by target molecules and the labelled molecules have been unable to bind to the immobilized molecules. An assay, which generates an inverse fluorescence signal response to the target molecule concentration in a sample, is called a competitive assay.

Another alternative assay is a non-competitive assay. In a non-competitive assay typically two binder molecules able to both simultaneously recognize a target molecule are employed. One of the molecules is immobilized onto a reaction vessel or another solid-phase. The molecules immobilized on the reaction vessel recognize the target molecules present in a sample and the target molecules will bind onto binding sites of the molecules immobilized onto the reaction vessel. The reaction vessel can now be optionally washed and all the target molecules not bound to binding sites are removed. Thereafter, the other binder molecule labelled with a fluorescent compound is added. This labelled binder molecule recognizes the bound target molecules and will bind to them at a different site than the binder molecules immobilized on the solid-phase. In case no target molecules are bound to the binding sites of the binder molecules immobilized on the reaction vessel, no labelled binder molecules are bound. The reaction vessel can be washed again to separate the bound and the non-bound labelled binder molecule. If the sample contained the target molecule, it was bound to the molecules immobilized on the reaction vessel and thereafter recognized by the labelled molecule. The formed layered complex is called as sandwich-structure. The measured fluorescence signal is relative to the target molecule concentration, and is high if a large amount or high concentration of the target molecule was present in the sample, and low if only a low concentration or small amount or none of the target molecule was present.

In both of the previous assays based on different principles at least a single wash or separation step is required before the fluorescence signal can be measured. This renders the assays complex and requires expensive instrumentation to carry out the assay automatically.

Homogeneous and Separation-free Assays

Fluorescence-phenomenon is associated with a property known as Foerster-type resonance energy transfer or fluorescence resonance energy transfer (FRET). In case, at a short distance, e.g. below 100 nm—preferably below 10 nm, from the fluorescent compound is present another fluorescent compound, which has an excitation wavelength almost equal to emission wavelength of the first fluorescent compound (known as spectral overlapping), the following can occur: the excited state of the first fluorescent compound is not released as radiative emission of a photon, but the excited-state is relaxed by transferring the energy to another fluorescent molecule, which is transferred to an excited state without absorption of a photon. The other fluorescent compound can thereafter release the excited state energy by emitting a photon at a wavelength characteristic to it. The emission wavelength of the other fluorescent compound is higher than the emission wavelength of the first fluorescent compound and some of the energy is lost in the process. The first fluorescent compound is called a donor and the other fluorescent compound an acceptor.

The energy-transfer process between donor and acceptor described above is called either Förster-type resonance energy-transfer or fluorescence resonance energy-transfer (FRET) and it can be utilized to convert the described heterogeneous and separation-based assays to homogeneous and separation-free assays. In homogeneous assays the binder molecules are not immobilized to solid-phase but labelled with the fluorescent compound typically acting as a donor while the second fluorescent compound present in the assay acts as an acceptor. Homogeneous assays based on FRET and lanthanide compounds as donors have been described by Mathis G, Clin Chem (1993) 39: 1953-1959, Rare earth cryptates and homogeneous fluoroimmunoassays with human sera; Blomberg, Hurskainen ja Hemmilä, Clin Chem (1999) 45:855-861, Terbium and rhodamine as labels in a homogeneous time-resolved fluorometric energy-transfer assay of the beta subunit of human chorionic gonadotropin in serum; Meyer, Haase, Hoheisel ja Bohmann WO 2004/096944, and Hemmilä, Hurskainen, Blomberg, Mukkala, Takalo, Kovanen ja Webb WO 98/15830. From publication Latva, Hemmilä, Blomberg ja Hurskainen U.S. Pat. No. 5,998,146 it is known also that spectral overlapping is not strictly required in case of lanthanide ions as donors. Common to all these assays is the use of long-lifetime fluorescent donor compounds, e.g. a lanthanide chelate, in combination with short-lifetime fluorescent acceptor compounds, i.e. so called prompt fluorescent compounds. In this case the fluorescence of the acceptor excited via fluorescence resonance energy transfer (so called sensitized acceptor emission) is also delayed and can be measured with temporal resolution.

Fluorescence Resonance Energy Transfer

Fluorescence resonance energy transfer (FRET) (Förster, T. Intermolecular energy migration and fluorescence. Ann. Physik 1948; 2, 55-75.) (or Förster resonance energy transfer) describes an energy transfer mechanism between two fluorescent molecules or between a fluorescent and a non-luminescent molecule. A fluorescent donor is excited at its specific fluorescence excitation wavelength. By a long-range dipole-dipole coupling mechanism, this excited state is then non-radiatively transferred to a second molecule, the acceptor, which is luminescent and can emit at its specific emission wavelength, or the quencher, which is non-luminescent or luminescent. The donor returns to the electronic ground state. The mechanism is widely employed in biomedical research (reviewed by Selvin P R. The renaissance of fluorescence resonance energy transfer. Nat Struct Biol 2000; 7: 730-734; and Lakowicz, J. Principles of fluorescence spectroscopy, 2nd edition. Plenum Press, New York, 1999).

The FRET efficiency is determined by the distance between the donor and the acceptor, the spectral overlap of the donor emission spectrum and the acceptor absorption spectrum, and the relative orientation of the donor emission dipole moment and the acceptor absorption dipole moment. The FRET efficiency E depends on the donor-to-acceptor distance r with an inverse 6th order law defined by $$E = 1/(1+(r/R_0)^6)$$

with $R_0$ being the Förster distance of this pair of donor and acceptor at which the energy transfer efficiency is 50%. The Förster distance depends on the overlap integral of the donor emission spectrum with the acceptor absorption spectrum and their mutual molecular orientation.

A process known as time-resolved fluorescence resonance energy transfer or TR-FRET has been developed to increase the signal to noise ratio of sensitized emission of the acceptor. TR-FRET uses lanthanide chelates, cryptates, ions or nanoparticles as donors. TR-FRET has specifically a problem with the measurement of the sensitized emission. As the excitation light source is turned off the original emission of the donor starts to decay exponentially and the energy-transfer further accelerates the decay. In TR-FRET based assays the sensitized emission of the acceptor has an apparent fluorescent lifetime typically much shorter than the lifetime of the donor. Especially, when the donor and acceptor are very close to each others (the FRET process has maximum efficiency) the sensitized acceptor emission can decay very fast, e.g. in a few microseconds instead of tens or hundreds of microseconds preferred for time-resolved detection. Typically, this results in a very weak emission from the acceptor. This has been tried to be solved by Kokko, Sandberg, Lövgren and Soukka [Europium(III)chelate-dyed nanoparticles as donors in a homogeneous proximity-based immunoassay for estradiol, Anal Chim Acta. 503:155-162 (2004)] by using europium chelate—dyed nanoparticles containing tens of thousands of europium chelates to increase the number of donors taking part in the FRET process in a single binding event. Another improvement has been described by Laitala (WO 2005/033709) optimizing the measurement time windows to very short delay. Ideally the sensitized emission of the acceptor should be measured simultaneously with the excitation of the donor, this is however not possible with time-resolved fluorescence.

Competitive Assay

In competitive assay the fluorescent donor compounds coupled to binder molecules are added to a reaction vessel. Target molecules present in sample compete in binding to binding sites of the binder molecules with derivatized analogues of target molecule labelled with fluorescent acceptor compound. The amount of labelled analogues bound to binder molecules has an inverse relationship to target molecules present in the sample. If no target molecules are present in the sample practically all binding sites of the binder molecules are occupied by the labelled analogues. In case of a very high concentration of target molecule present in the sample, the binding sites of the binder molecule are occupied by the target molecules and not available for binding of the labelled analogue. The components of the assay can be added in a single or multiple steps and optionally the assay can be also incubated between the additions.

The FRET-process is only possible when the donor and acceptor are at a short distance from each other, which is true only when the acceptor labelled analogue is bound to the binder molecule conjugated to the donor. Thus the maximum sensitized acceptor emission is produced when the target molecules are not present in the sample or their concentration is very small and the sensitized acceptor emission decreases with increasing concentration of target molecule, which is typical for the competitive assay principle.

Non-competitive Assay

In non-competitive assay two kinds of binder molecules, first labelled with donor and second labelled with acceptor are added to a reaction vessel. Both of the binder molecules are able to bind simultaneous to the target molecule, i.e. they recognize and bind to different site of the target molecule. When a sample is added the labelled binder molecules present in excess recognize the target molecules and complexes containing the first and second binder as well as analyte are formed—this complex wherein the target molecule is between the two binder molecules is called a sandwich-structure. One of the binder molecules is labelled with the donor and the second with the acceptor and the complex contains both the donor and acceptor label within a short distance from each other enabling the FRET-process between the donor and the acceptor. The formation of the complex and thus the measured sensitized acceptor emission is relative to the presence of the target molecule in the sample. In case no target molecule is present in the sample, no complexes are formed. Also in this assay the components of the assay can be added in a single or multiple steps and optionally the assay can be also incubated between the additions.

Problems in Bioassays Based on FRET Process

In a normal FRET assay only the sensitized emission of the acceptor is measured at an acceptor specific emission wavelength. If the sample has absorbance at this wavelength also the emission of the donor can be measured. Assuming that the absorption is equal at the wavelength of the donor emission and the wavelength of sensitized acceptor emission, the ratio between the donor and the sensitized acceptor emission is independent on the absorption. Donor concentration in all samples is equal and thus, if only a small amount of donors participate in the FRET process, the donor emission can be considered as an internal standard. Alternatively, the donor emission measured from the sample compared to donor emission from a reference sample with no absorbance can be used as a correction factor to estimate the true sensitized emission in the actual sample. These methods have been described in U.S. Pat. Nos. 5,527,684 and 6,352,672 by Mabile et. al. They correct also the variation of absorption at wavelength of excitation.

Another problem in the FRET-based bioassays is radiative energy-transfer. The normal radiative emission of the donor can be reabsorbed by acceptor molecules not at short distance from the donor (unable to participate in the FRET-process) according to Beer-Lambert law and these acceptors generate delayed emission at acceptor specific wavelength. This emission is called radiative energy transfer or non-proximity energy transfer and causes unwanted background to the measured signal. As the emission wavelength is at the acceptor maximum this cannot be spectrally eliminated. However, the apparent decay time of the radiative energy transfer is typically equal to the lifetime of the donor in absence of the acceptor, and thus longer than the apparent lifetime of the sensitized acceptor emission due to FRET. The excited state of the long-lifetime luminescent donor participating in the FRET process is released by two competing processes—the radiative decay typical to the donor and the FRET process, whereof the first is typically constant but the second decay is strongly dependent on the distance between the donor and the acceptor. This results in that the observed apparent radiative decay of the donor participating in FRET is equal or faster than the decay of the donor alone but slower than the observed apparent decay of the sensitized acceptor emission. Thus, effective energy transfer to the acceptor releases the donor excitation state faster than its own characteristic long-lifetime emission. The greater the FRET efficiency is the shorter the observed apparent decay of the donor will be.

Radiative energy transfer process life-time can still be considered practically equal to the donors own characteristic long-lifetime emission because typically most of the signal due to radiative energy transfer is generated by donors not participating in energy transfer—this is especially true when the binder labelled with the donor is used in a large excess to the target molecule, which is typically in a non-competitive assay.

Perhaps the greatest problem of using time-resolved fluorescence in FRET type assays is due to the fact that after the excitation light pulse has been turned of the emission drops exponentially. Even though this creates better signal to noise ratios than in direct fluorescent measurement, the temporal resolution drops the fluorescent signal of the acceptor dramatically.

Known Use of the FRET Process

The FRET process was first used in homogenous assays by Ullman [Ullman, E. F., Schwarzberg, M., and Rubenstein, K. E. (1976) Fluorescent excitation transfer immunoassay. A general method for determination of antigens. J. Biol. Chem. 251, 4172-4178]. He used traditional (short-lifetime, i.e. prompt fluorescent) fluorescent molecules as donors and acceptors. FRET process has been used also with time-resolved fluorescent labels. The described methods, however, suffer the problems associated with traditional fluorescence and time-resolved fluorescence. Anti-Stokes photoluminescence labels as donors in the FRET process are described by Soukka, Härmä and Lövgren in WO 2004/086049. This publication also describes the unwanted background signal originating from the radiative energy transfer. Anti-Stokes FRET is also described in detail in Immunoassay designs and potential of particulate photoluminescent lanthanide reporters, Soukka, 2003; Gillot Oy, Turku, Suomi; ISBN 951-29-2393-9. The publication also lists long-lifetime anti-Stokes photoluminescent donors, short-lived acceptors and a method of measurement.

From the publications Laitala WO 2005/033709 and Ming, Rev Sci Instr (1999), 70:3877-3881. An Improved instrument for measuring time-resolved lanthanide emission and resonance energy transfer; it is known that when a traditional long-lifetime (down-converting) photoluminescent donor and a short lived acceptor is used, optimal measurement is performed as soon as possible after the excitation light pulse has been turned off.

OBJECT AND SUMMARY OF THE INVENTION

One object of the present invention is to provide a method to correct for error in an anti-Stokes photoluminescence measurement in a Foerster-type resonance energy-transfer assay.

Another object of the present invention is to provide a use of a device for correcting for error in an anti-Stokes photoluminescence measurement in a Foerster-type resonance energy-transfer assay.

A further object of the present invention is to provide a system for carrying out a method to correct for error in an anti-Stokes photoluminescence measurement in a Foerster-type resonance energy-transfer assay.

Yet another object of the present invention is to provide a software product for the system for carrying out a method to correct for error in an anti-Stokes photoluminescence measurement in a Foerster-type resonance energy-transfer assay.

The present invention provides a method to correct for error in an anti-Stokes photoluminescence measurement in a Foerster-type resonance energy-transfer assay. The method comprises the following steps a) exciting anti-Stokes photoluminescent molecules, ions, phosphors, chelates, or particles, i.e. donors of said assay, with one wavelength or multiple wavelengths of light wherein said wavelength or wavelengths are greater than that of an emission wavelength of acceptor molecules in said assay, b) measuring emission light signal at a wavelength, which is said emission wavelength of said acceptor molecules in said Foerster-type resonance energy-transfer assay, and which differs from the emission wavelength of said anti-Stokes photoluminescent donor, in at least two different time windows, i) a first time window within the time window defined by the excitation light pulse, i.e. within the time window opening when the excitation light pulse is switched on and closing when the excitation light pulse is switched off, and ii) a second time window to follow the first time window not at all overlapping with said time window defined by the excitation pulse, and c) correcting the emission light signal measured, comprising signals originating from non-radiative and radiative energy transfer, within the first time window by estimating the ratio of the signals from non-radiative and radiative energy transfer or the signal originating from radiative energy transfer using at least one emission light signal measured in said second time window.

The present invention also provides use of a device for carrying out the method according to the invention. The device comprises a) a light source, with means for turning said light source on and off either electrically or mechanically, emitting light of a wavelength that is ≧800 nm, and
b) a detector with means for detecting light of a selected wavelength as a function of time in at least two time windows.

The present invention further provides a system for carrying out the method of the invention. The system comprises
a) a light source, with means for turning said light source on and off either electrically or mechanically, emitting light of a wavelength that is ≧800 nm, and
b) a detector with means for detecting light of a selected wavelength as a function of time in at least two time windows.

Characteristic for the system is that it further comprises a data processing unit with software for correcting an emission light signal measured within a first time window within the time window defined by an excitation light pulse, i.e. within a time window opening when the excitation light pulse is switched on and closing when the excitation light pulse is switched off, with an emission light signal measured within a second time window to follow the first time window not at all overlapping with said time window defined by the excitation pulse.

The present invention yet provides a software product for the system of the invention. Characteristic for the software product is that it comprises means for correcting an emission light signal measured within a first time window within the time window defined by an excitation light pulse, i.e. within a time window opening when the excitation light pulse is switched on and closing when the excitation light pulse is switched off, with an emission light signal measured within a second time window to follow the first time window not at all overlapping with said time window defined by the excitation pulse.

DETAILED DESCRIPTION OF THE INVENTION

Figure 1A:
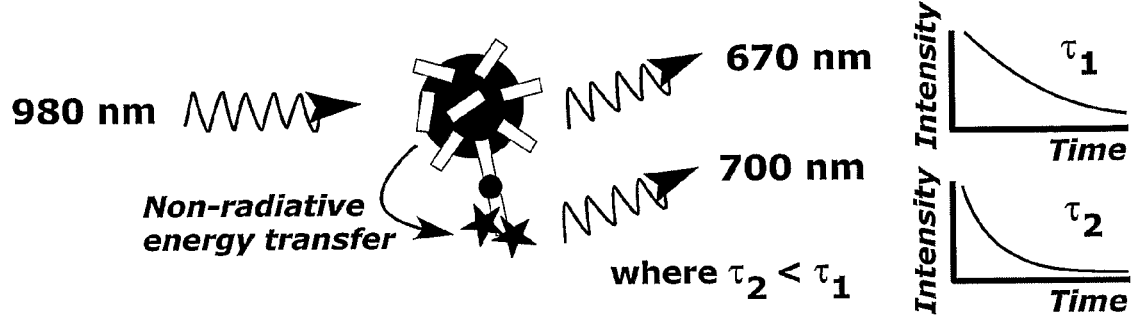
FIGS. 1a and 1b illustrate the differences in lifetimes of the sensitized acceptor emission ($\tau_2$; non-radiative energy transfer) and radiative background emission ($\tau_3$; reabsorption of emitted light).

Prior are does not describe correction of the sensitized acceptor emission measured without temporal resolution (i.e. simultaneously with excitation) by using a temporal resolution and a life-time analysis of the delayed sensitized acceptor emission signal (measured with a delay after excitation) to separate emission originating from radiative energy transfer and FRET in the signal measured without temporal resolution. What is not known from prior art is that when anti-Stokes photoluminescent donor is used the measurement of the sensitized acceptor emission can be performed simultaneously with the excitation light pulse. This is possible because the measurement does not need to be delayed to reduce the background, as is the case in time resolved fluorescence. Furthermore with the simultaneous continuous excitation and photon counting the donor can be excited again immediately after the excited state of the donor is relaxed. This has not been disclosed in prior art, but is especially advantageous and further improves the performance of the FRET-based assay, because the excited state of the donor is relaxed much sooner when the donor participates in energy transfer to the acceptor. This both increases total signal per time and improves the signal to background ratio.

The purpose of this invention is to correct for the errors described earlier and improve the performance of anti-Stokes photoluminescent Foerster-type resonance energy-transfer assay. In more detail, the purpose of the method of correction described is to subtract the signal due to radiative energy transfer in signal measured in Foerster-type resonance energy-transfer assay using anti-Stokes photoluminescent donor. Furthermore the purpose of this invention is to create a measurement device with such a correction feature, so that the performance of anti-Stokes photoluminescent Foerster-type resonance energy-transfer assay can be improved.

Definitions

"Prompt photoluminescence" means photoluminescence, which is measured simultaneously while the excitation light source illuminates the object, sample or solution being measured. The internal lifetime of this prompt photoluminescence is typically less than 1 μs (microsecond), preferably less than 100 ns (nanoseconds), and thus, in principle, a single molecule can be excited over one million times per second under suitable conditions. A molecule with prompt photoluminescence is called a short-lifetime emission fluorescent molecule. A long-lifetime fluorescent molecule is a fluorescent or photoluminescent molecule with an emission lifetime of typically over 1 μs, preferably more than 10 μs. The photoluminescence of both a short-lifetime and a long-lifetime photoluminescent molecule can be measured with temporal resolution, but temporal resolution provides less advantages with a short-lifetime photoluminescence molecule because autofluorescence and other background photoluminescence typically has a lifetime equal to short-lifetime photoluminescent molecules and thus background reduction is not possible.

The term "homogeneous bioassay" shall be understood to cover bioassays such as e.g. immunoassays, nucleic acid hybridization assays, ligand binding assays and enzyme activity assays, requiring no separation steps. Single or multiple steps of each; addition of reagents, incubation and measurement are the only steps required.

The term "separation step" shall be understood to be a step where a labelled bioassay reagent bound onto a solid-phase, such as for example a microparticle or a microtitration well, is separated and physically isolated from the unbound labelled bioassay reagent; for example the microtitration well is washed (liquid is taken out and, to improve the separation, additional liquid is added and the well emptied) resulting in separation of the solid-phase bound labelled bioassay reagent from the labelled bioassay reagent not bound onto the solid-phase.

The term "fluorescence" shall be understood to cover photoluminescence, i.e. luminescence excited by light, fluorescence, including delayed fluorescence with microsecond or millisecond fluorescence lifetime, ionic photoluminescence, up conversion based anti-Stokes photoluminescence, and phosphorescence. In addition, the term shall cover electrogenerated luminescence and electrochemiluminescence.

The term "fluorescent label" or "fluorescent compound" shall be understood to cover dye molecules, proteins, polymers, particles, dyed particles and phosphors, which express fluorescence.

The terms "acceptor" and "donor" shall be understood to cover fluorescent compounds, which participate in energy transfer processes with another fluorescent compound or a non-luminescent compound.

The terms "non-luminescent" and "non-fluorescent" shall be understood as property of a light absorbing compound not to produce any or a significant amount of luminescence when excited and relaxing from the excited-state. In contrast to luminescent compounds, the excited-state energy of a non-luminescent compound is predominantly relaxed via non-radiative pathways, typically producing heat instead of light. The fluorescence quantum yield of a non-luminescent compound is very poor, typically below 5 percent. Examples of non-luminescent compounds are quencher compounds, which can efficiently participate in energy transfer from a fluorescent compound, but which do not produce any significant luminescence upon excitation.

The term "long-lifetime fluorescence" and "long-lifetime fluorescent compound" shall be understood to cover fluorescence and fluorescent compounds having a luminescence lifetime equal to or more than 1 microsecond (the lifetime being calculated as the time wherein luminescence emission intensity decays to the relative value of 1/e, i.e. to approximately 37% of the original luminescence emission intensity). The compounds capable of long-lifetime fluorescence include, but are not limited to, lanthanide chelates, lanthanide-chelate dyed-nanoparticles, lanthanide phosphors and nanophosphors, porphyrins, and porphyrin dyed-nanoparticles.

The term "light" and "excitation light" and "emission light" shall be understood as electromagnetic radiation at wavelengths from 200 nm to 1600 nm. These wavelengths cover ultraviolet, near-ultraviolet, visible, near-infrared and infrared light.

The term "short-lifetime fluorescence" and "short-lifetime fluorescent compound" shall be understood to cover fluorescence and fluorescent compounds with a luminescence lifetime of less than 1 microsecond.

The terms "acceptor", "acceptor label" and "acceptor compound" mean luminescent or non-luminescent compounds having typically, but not necessarily, absorption spectra at least partially overlapping with the emission spectra of the donor and essentially capable of energy transfer from the donor.

The terms "donor" and "donor label" shall be understood as fluorescent compounds capable of energy transfer either to an acceptor or quencher compound.

The terms "sensitized emission" and "sensitized acceptor emission" shall be understood as emission of the acceptor label generated by energy transfer from the donor label in proximity upon excitation of the donor label. In case of long-lifetime donor label the sensitized emission has also prolonged fluorescence lifetime. Further, the sensitized emission shall also be understood to cover values of sensitized emission corrected by for example measurement of the donor emission or sample absorbance, or values indicating any ratio of the donor emission and the sensitized emission.

The term "up-conversion fluorescence" and "up-conversion fluorescent compound" means fluorescence produced by and fluorescent compounds converting lower energy incident light to higher energy emitted light. It is also called anti-Stokes fluorescence or anti-Stokes photoluminescence. Anti-stokes photoluminescence material converts low energy light to high energy light. In "up-conversion fluorescence" two or more lower energy photons of the same or different energy are absorbed sequentially, in two or more stages, to generate a single higher energy photon, contrary to simultaneous absorption in two-photon or multi-photon excitation.

The term "up-converting luminescent label" and "up-converting lanthanide label" shall be understood as up-conversion fluorescent compound, i.e. luminescent lanthanide label being able to up-convert a lower energy excitation to a higher-energy emission based on an excitation in two or more stages; meaning that two or more photons are sequentially absorbed to excite the label contrary to simultaneous absorption in two or multi photon excitation. The up-converting lanthanide labels include up-converting lanthanide phosphors and up-converting lanthanide chelates.

The term "up-converting lanthanide chelate" in this context means an up converting lanthanide label, where a single rare earth ion or a combination of different rare earth ions is chelated to a mono or multinuclear complexing ligand. The ligand may or may not contain a light harvesting structure. The light collection efficiency of individual ions and chelated ligands without a light harvesting structure is poor. Therefore, up-converting rare earth chelates can be designed to contain a ligand with light-harvesting organic or inorganic structures, e.g. another ion, incorporated. The collected energies of two or more photons are transferred one after another by intramolecular nonradiative processes from the singlet to the triplet state of the organic structure, then from the triplet state sequentially to the emissive level of the rare earth ion, which then emits a single photon of characteristic emission.

The term "up-converting lanthanide phosphor" shall be understood as a particulate luminescent lanthanide label capable of up-conversion, wherein a particulate absorbs long wavelength radiation and emits light at shorter wavelength as result of energy pooling of sequential absorption of long wavelength radiation. In certain types of phosphors, a priming dose of energy at shorter wavelength is required to excite and pre-load the phosphor before the up-conversion of long wavelength radiation is possible. The up-converting phosphor can be able to delocalise its excitation from a part or the entire volume of the particulate by internal transfer of energy between similar excited states within the particulate to a single or a few acceptor molecules. This means that a single acceptor can be excited by lanthanides which would otherwise be too far away for energy transfer to be efficient. The diameter of the particulate phosphor is preferable equal or greater than 4 nm and preferably smaller than 10 µm, more preferably smaller than 1 µm.

The terms "energy transfer", "fluorescence energy transfer" and "FRET" shall be understood as transfer of excited state energy from donor compound to acceptor or quencher compound in proximity. Typically the energy transfer is based on Forster type fluorescence resonance energy transfer, but especially in case of lanthanide labels other mechanism can be prevalent.

Preferred Embodiments of the Invention

In a preferred embodiment of the method according to the invention the second time window is within a third time window and said third time window opens as soon as the excitation light pulse has died out; preferably 10 µs, more preferably 3 µs and most preferably 1 µs after having shut off the excitation light pulse; and said third time window closes before two lifetimes of the emission of the acceptor resulting from non-radiative energy transfer, i.e. Foerster type resonance energy transfer from said donor to said acceptor, i.e. $2\tau_2$, has passed from shutting off the excitation light pulse.

In another preferred embodiment of he method according to the invention the second time window is within a fourth time window, which opens when at least two lifetimes of the emission of the acceptor resulting from non-radiative energy transfer, i.e. Foerster type resonance energy transfer from said donor to said acceptor, i.e. $2\tau_2$, has passed from shutting off the excitation light pulse and closes before or when four lifetimes, preferably three lifetimes, and more preferably two lifetimes, of the emission of the acceptor resulting from radiative energy transfer, i.e. from reabsorbtion by the acceptor of light emitted by the donor, i.e. $4\tau_3$, $3\tau_3$ and $2\tau_3$ correspondingly, has passed from shutting off the excitation light pulse.

In a further preferred embodiment according to both above preferred embodiments of the method according to the invention the emission light is measured in at least three different time windows: the first time window, within the time window defined by the excitation light pulse; the third time window, which opens as soon as the excitation light pulse has died out and closes before two lifetimes of the emission of the acceptor resulting from non-radiative energy transfer, i.e. $2\tau_2$, has passed from shutting off the excitation light pulse; and the fourth time window, which opens when at least two lifetimes of the emission of the acceptor resulting from non-radiative energy transfer, i.e. $2\tau_2$, has passed from shutting off the excitation light pulse and closes before or when four lifetimes, preferably three lifetimes, and more preferably two lifetimes, of the emission of the acceptor resulting from radiative energy transfer, i.e. from reabsorbtion by the acceptor of light emitted by the donor, i.e. $4\tau_3$, $3\tau_3$ and $2\tau_3$ correspondingly, has passed from shutting off the excitation light pulse.

In some preferred embodiment of the method of the invention emission light is measured in more than three different time windows comprising multiple measurements in 1 to 100 µs increments within the second time window. The multiple measurements in the 1 to 100 µs increments can be carried out in time windows three and/or four. The multiple measurements in the 1 to 100 µs increments are preferably carried out in a fifth time window which opens as soon as the excitation light pulse has died out, preferably about 1 µs after having shut off the excitation light pulse; and closes when about 50 ms, preferably 20 ms, and more preferably 5 ms has passed from shutting off the excitation light pulse.

Features of a typical embodiment of the correction method are:

anti-Stokes photoluminescent molecules, ions, phosphors, chelates, or particles are excited with one or multiple wavelengths of light with a wavelength greater than that of the emission wavelength of the acceptor molecules (e.g. small molecule fluorescent dyes, inorganic particles or dyed fluorescent particles) in a Foerster-type resonance energy-transfer assay, emission light is measured in a wavelength region, which corresponds to that of the emission wavelength of the said acceptor molecules in a Foerster-type resonance energy-transfer assay, and which is different to that of the emission of the anti-Stokes photoluminescent donor, and emission light is measured in at least two different time windows, so that one time window is simultaneous to the excitation light pulse and at least one time window is delayed (i.e. measured after the excitation pulse) not overlapping the time window simultaneous to the excitation light.

The emission signal measured simultaneously with the excitation light pulse is corrected with at least one signal measured in the delayed window.

This invention also relates to a measurement device, which enables correction according to the method of the invention. Characteristic features of a typical embodiment of the measurement device are:

that the measurement device has a light source used to excite the anti-Stokes photoluminescent molecules, ions, chelates, phosphors or particles so that the time the excitation light illuminates the object, sample or solution to be measured can be controlled, that the wavelength of the excitation light source is greater than that of the emission wavelength of the acceptor molecules, ions or particles in a Foerster-type resonance energy-transfer assay, that the measurement device has means to select measured wavelength so that it corresponds to that of the emission wavelength of the acceptor molecules in a Foerster-type resonance energy-transfer assay, and that the measurement device has means to detect the emission light and study it as function of time.

Description of the Drawings

FIGS. 1-4 describe the correction method according to the invention to subtract the signal originating the radiative energy transfer in signal of the anti-Stokes photoluminescent Foerster-type resonance energy-transfer assay. In addition, an instrument capable to collecting the signals required to performed the correction in anti-Stokes photoluminescent Foerster-type resonance energy-transfer assay is described.

Figure 1B:
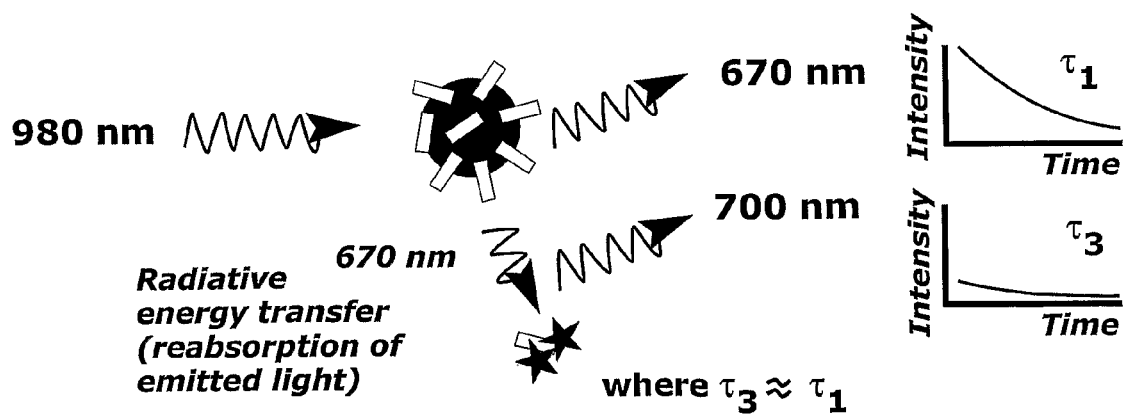

In particular, sensitivity of the rapid assays utilizing high concentration of the labelled components is restricted by the luminescence background at acceptor specific wavelength resulting from radiative energy transfer between donor and acceptor labels in solution, as illustrated in FIG. 1. The light emission resulting from radiative and nonradiative energy transfer, respectively, differ in their lifetimes, $\tau_3$ and $\tau_2$, respectively, and the radiative energy transfer can be excluded with temporal resolution and separation of components of different lifetimes in luminescence emission. The luminescence lifetime of the light emission resulting from non-radiative energy transfer ($\tau_2$) is shorter (Heyduk T and Heyduk E, Anal Biochem 2001; 289:60-67; Selvin PR et al., J Am Chem Soc 1994;116:6029-6030) than the lifetime of the light emission from the radiative energy transfer ($\tau_3$) and direct emission of the donor ($\tau_1$).

Figure 2:
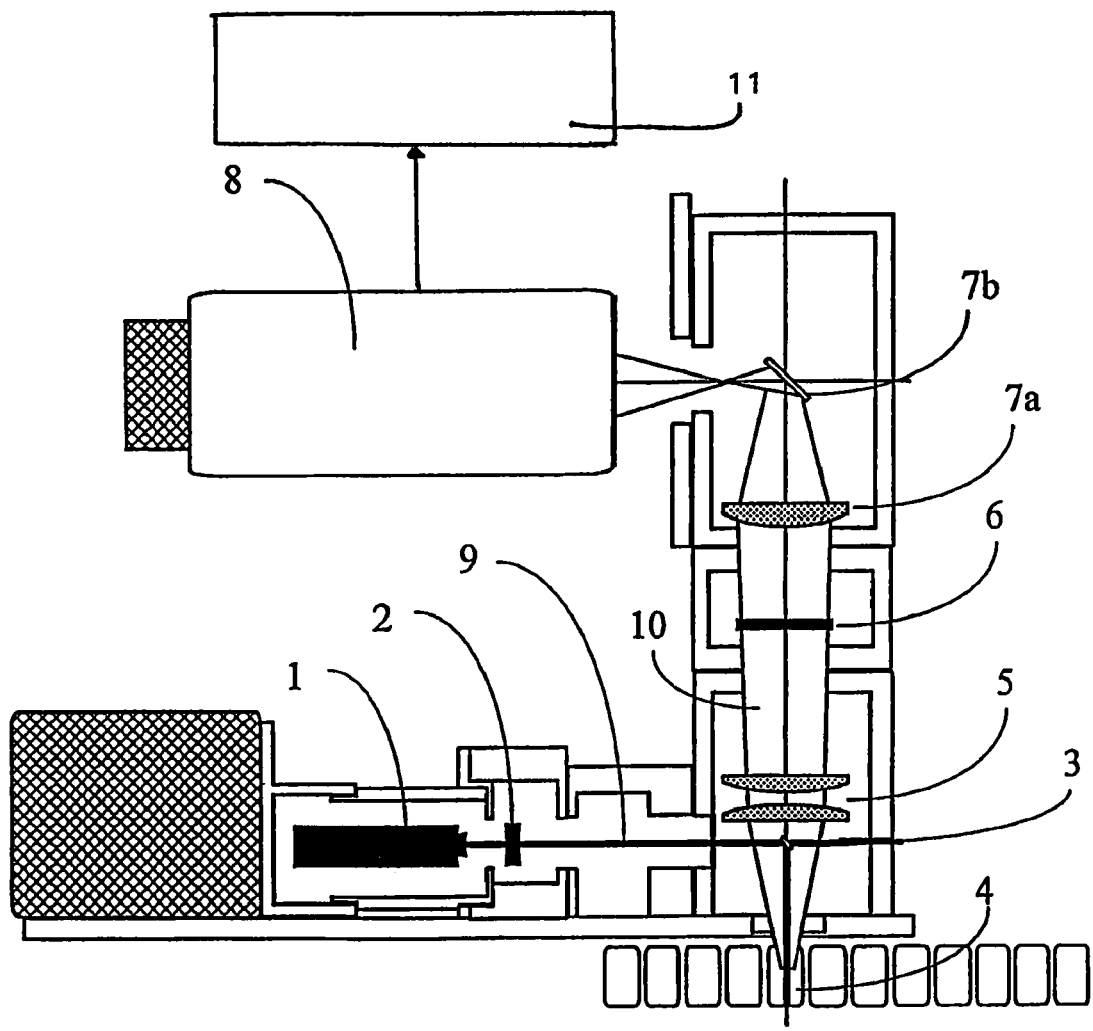
FIG. 2 illustrates an example of a measurement device structure.

FIG. 2 illustrates an example of a measurement instrument, which can measure the emission wavelength intensity of the acceptor molecules in a Foerster-type resonance energy-transfer assay, where the FRET process is induced with anti-Stokes photoluminescent donors. The measurement is carried out as follows: The laser diode is switched on for a duration of for example 1 ms. The light emitted by the laser excites the anti-Stokes photoluminescent donors. The donors transfer the excitation energy according to the FRET process to the acceptors in close vicinity and the acceptor molecules emit photons at their own characteristic emission wavelength. The wavelength of the emission light is selected so that only characteristic acceptor emission is measured.

The device of FIG. 2 comprises an excitation light source, i.e. a diode laser module 1, which emits light at 980 nm wavelength. An optical filter component 2 blocks all other wavelengths emitting from the light source (e.g. long-pass filter with edge wavelength sufficiently below the laser wavelength). A mirror 3 directs the excitation light to the sample in sample container 4. Mirror 3 is a small-diameter full mirror, a dichroic mirror or half pass mirror. Sample container 4 is a microtiter plate or cuvette. Lenses 5 collect the emission light from the sample to the optical filter 6, which selects the wavelength so that donor emission is blocked and that acceptor emission passes to the detector 8; the filter blocks also the wavelength of the excitation light. Detector 8 is a photodetector, which can detect light as a function of time, e.g. a photomultiplier tube operated in photon counting mode, and is operatively connected to data processing unit 11. The path travelled by excitation light is indicated with 9. The path travelled by emission light is indicated with 10.

Figure 3:
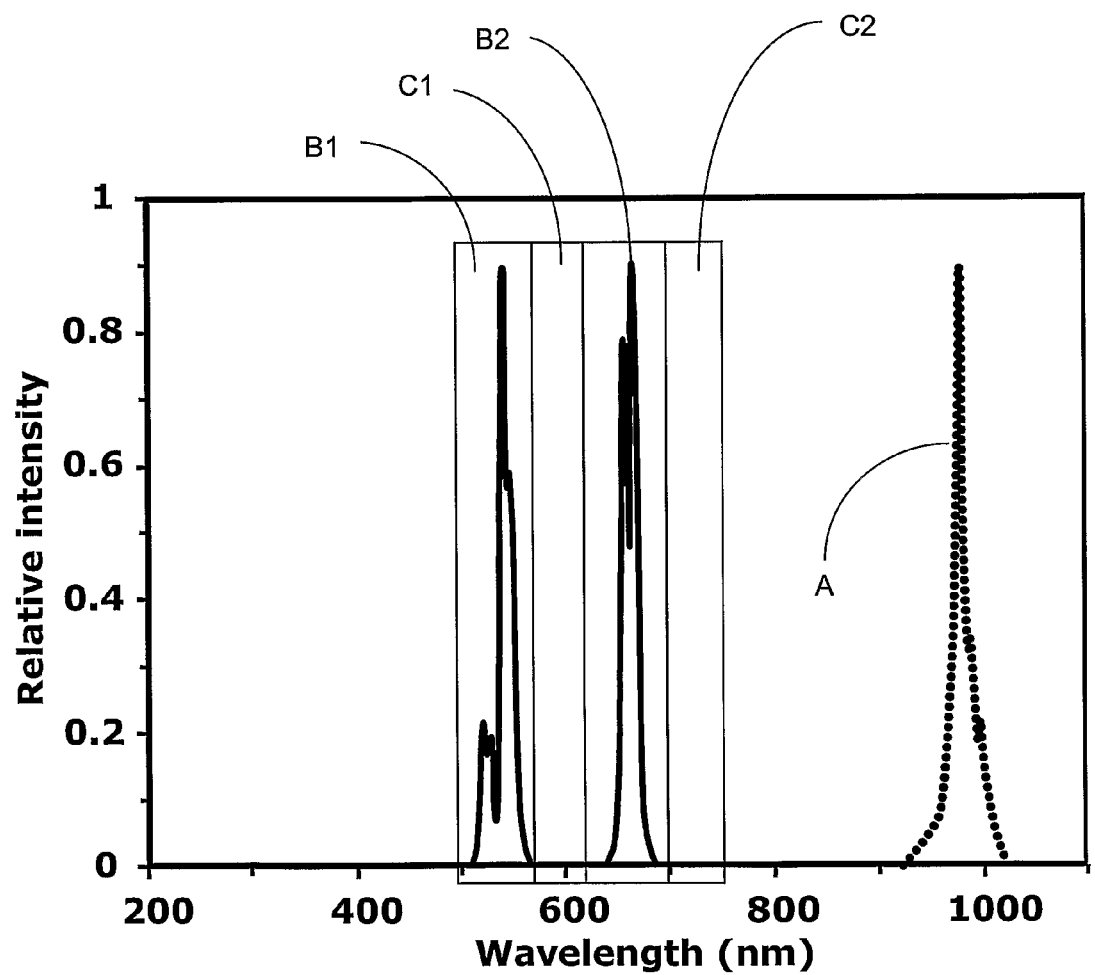
FIG. 3 illustrates examples of wavelengths of both anti-Stokes photoluminescent donors and wavelength areas of possible acceptor emission peaks.

FIG. 3 shows an example of excitation and emission wavelengths of an anti-Stokes photoluminescent donor. The peak of the intensity maximum of the excitation wavelength is indicated with A. In this example erbium and ytterbium based phosphor is used as donor. The donor has an emission intensity maxima B1 at wavelength 550 nm and B2 at 670 nm. According to the setup in FIG. 3 the measurement device measures emission intensity in wavelength areas C1 and C2. So that C1 is higher than B1 between 580 to 620 nm. Correspondingly C2 is higher than B2 between 700 to 750 nm. Areas C1 and C2 are optimal emission maxima for FRET process acceptor fluorophores.

The instrumentation in FIG. 2 measures first prompt fluorescence. The signal is measured simultaneously with the excitation light pulse. After the light pulse has been turned off the long-lifetime or delayed component of the fluorescence is measured and used to correct the prompt component. In an example setup the instrument excitation light source a laser is turned on for 1 ms. During this time the emission signal is integrated. After this the light source is turned off. However the emission signal is still measured in 10 μs increments for the next 20 ms. The results of individual signals for 10 μs time windows are stored to a random access memory to allow integration of any time window within this time scale, i.e. between 0 and 20 ms with 10 μs resolution.

Figure 4:
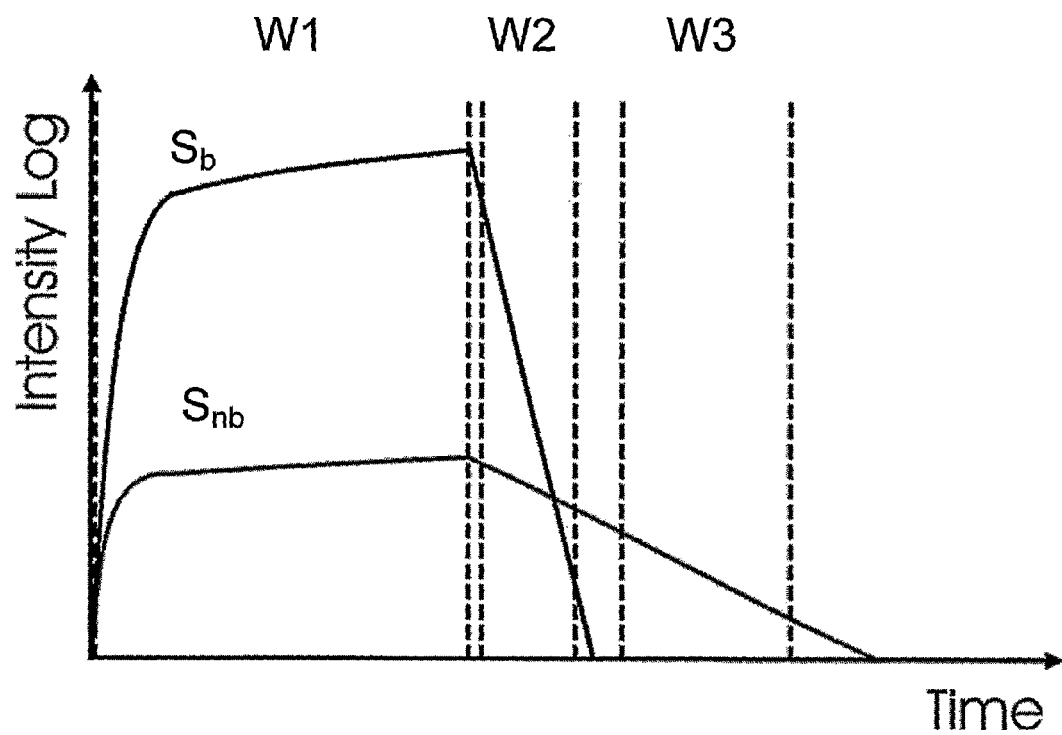
FIG. 4 illustrates Foerster-type resonance energy transfer acceptor emission intensity and the radiant energy transfer induced acceptor emission intensity in logarithmic scale as a function of time, and the distinct difference in lifetimes between the two intensities.

FIG. 4 shows the FRET acceptor emission measured at the characteristic wavelength as a function of time in logarithmic scale. Curve $S_b$ shows the Foerster-type resonance energy transfer signal.

Time window W1 is the time when excitation light source is on. The strength of signal $S_b$ depends on the amount of Foerster-type resonance energy transfer that takes place in the sample container. The sample also gives out signal $S_{nb}$, which corresponds to the radiative energy transfer. Signal $S_{nb}$ is unwanted background created by the unbound components and not originating from the FRET process. $S_{nb}$ increases the background and reduces the signal to background ratio of the assay.

Time window W3 shows only curve $S_{nb}$ because it has a longer time constant than $S_b$. The amount of $S_{nb}$ in time window W3 can be used to estimate the amount of $S_{nb}$ in time window W1. The estimated amount of $S_{nb}$ in time window W1 can then be reduced from the total signal integrated in time window W1, thus correcting the error caused by radiant energy transfer to the total signal of the Foerster-type resonance energy transfer signal.

We have now described a method to correct for the radiant energy transfer component in a FRET type assay. Characteristic features of the invention are that total signal can be measured with simultaneous excitation (without temporal resolution) and that the component originating from the radiative energy transfer in the measured total signal can be subtracted by measuring a long-lifetime or delayed photoluminescent component.

According to one embodiment of the invention, the instrument measures prompt photoluminescence and time resolved long-lifetime photoluminescence in at least two different time windows W1 and W3 shown in FIG. 4. Time window W3 shows only the long-lifetime photoluminescent component $S_{nb}$ caused by radiative energy transfer because it has longer apparent time constant. The form of the $S_{nb}$ curve is unchanged because the time constant remains the same. Time window W1 shows the sum of signals $S_b$, caused by the Foerster-type resonance energy transfer process, and $S_{nb}$ originating from the radiative energy transfer.

The ratio of the $S_{nb}$ value in window W3 to the $S_{nb}$ value in W1 is constant, thus the amount of $S_{nb}$ in W3 can be used to indicate the amount of $S_{nb}$ in W1. When the total $S_{nb}$ in window W3 is known, the real signal $S_b$ in window W1 can be estimated. This is done by reducing the estimated signal $S_{nb}$ in W1 from the total signal in W1.

In an actual assay a sample with anti-Stokes photoluminescent donor and acceptor where the binding of the two to a distance of preferably below 10 nm of each other required by FRET is blocked. As a result only radiative energy transfer takes place. A signal, which only consists of $S_{nb}$, is measured in W1 and W3, and a ratio of the two is calculated. For all other samples the amount of $S_{nb}$ in W1 can be estimated by multiplying the $S_{nb}$ measured in W3 with the ratio measured in the reference sample.

If all the components in the assay remain constant also the ratio of $S_{nb}$ in W1 to $S_{nb}$ in W3 remains constant. In this case the ratio can be determined prior to performing the assay and stored into instrument memory.

In FIG. 4 the signal in window W1 comprises both the signal of the bound label $S_b$ and that of the non-bound label $S_{nb}$. The signal in window W3 mainly comprises only the signal of the non-bound label. Therefore, a useful output signal S, indicative of the bound label $S_b$ (in window W1), can be expressed by formula (I):

$$S = S_b = S_{W1} - k \cdot S_{W3} \quad (I)$$

Where SW1 and SW3 denote signals in window W1 and window W3, respectively, and k is a constant depending on the label system used and the widths of windows W1 and W3. Obviously, k is obtained by first measuring a sample with only non-bound label (no bound label present). If no bound label is present $k = (S_{W1}/S_{W3})_{nb}$ and the value obtained for k can then be used for subsequent test samples.

A useful ratio bound signal to non-bound signal, Sb/Snb, can be determined based on the above using formula (II):

$$S_b/S_{nb} = (S_{W1} - k \cdot S_{W3})/S_{W3} \quad (II)$$

A more sophisticated system can be obtained by employing several windows after the excitation light is switched off. For example, with several 1-20 μs wide successive windows, it is possible to determine the decay curves of the bound and non-bound signals. These curves are helpful when investigating and developing new label compounds the decay characteristics of which are yet unknown. The decay curve of a non-bound label can for example be extrapolated to evaluate the non-bound signal in widow W1 when the excitation light is on.

The invention also describes a measurement device used to measure homogenous anti-Stokes photoluminescent Foerster-type resonance energy-transfer assays.

It will be appreciated that the methods and devices of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

The invention claimed is:

1. A method to correct for error in an anti-Stokes photoluminescence measurement in a Foerster-type resonance energy-transfer assay, comprising the following steps
   a) exciting anti-Stokes photoluminescent molecules, ions, phosphors, chelates, or particles, with one wavelength or multiple wavelengths of light wherein said wavelength or wavelengths are greater than that of an emission wavelength of acceptor molecules in said assay,
   b) measuring emission light signal at a wavelength, which is said emission wavelength of said acceptor molecules in said Foerster-type resonance energy-transfer assay, and which differs from the emission wavelength of said anti-Stokes photoluminescent donor, in at least two different time windows,
      i) a first time window within the time window defined by the excitation light pulse, and
      ii) a second time window to follow the first time window not at all overlapping with said time window defined by the excitation pulse, and
   c) correcting the emission light signal measured, comprising signals originating from non-radiative and radiative energy transfer, within the first time window by estimating the ratio of the signals from non-radiative and radiative energy transfer or the signal originating from radiative energy transfer using at least one emission light signal measured in said second time window.

2. The method according to claim 1 wherein the second time window is within a third time window and said third time window opens as soon as the excitation light pulse has died out; and said third time window closes before two lifetimes of the emission of the acceptor resulting from non-radiative energy transfer, has passed from shutting off the excitation light pulse.

3. The method according to claim 1 wherein the second time window is within a fourth time window, which opens when at least two lifetimes of the emission of the acceptor resulting from non-radiative energy transfer, has passed from shutting off the excitation light pulse and closes before or when four lifetimes, of the emission of the acceptor resulting from radiative energy transfer has passed from shutting off the excitation light pulse.

4. The method according to claim 2 wherein said emission light is measured in at least three different time windows: the first time window, within the time window defined by the excitation light pulse; the third time window, which opens as soon as the excitation light pulse has died out and closes before two lifetimes of the emission of the acceptor resulting from non-radiative energy transfer; and the fourth time window, which opens when at least two lifetimes of the emission of the acceptor resulting from non-radiative energy transfer, has passed from shutting off the excitation light pulse and closes before or when four lifetimes of the emission of the acceptor resulting from radiative energy transfer has passed from shutting off the excitation light pulse.

5. The method according to claim 1 wherein emission light is measured in more than three different time windows comprising multiple measurements in 1 to 100 μs increments within the second time window.

6. The method according to claim 5 wherein the multiple measurements in the 1 to 100 μs increments are carried out in the third and/or a fourth time window.

7. The method according to claim 5 wherein the multiple measurements in the 1 to 100 μs increments are carried out in a fifth time window which opens as soon as the excitation light pulse has died out and closes when about 50 ms, has passed from shutting off the excitation light pulse.

8. A system for carrying out the method according to claim 1, which system comprises
   a) a light source, capable of being turned on and off either electrically or mechanically, and emitting light of a wavelength that is $\geq 800$ nm, and
   b) a detector capable of detecting light of a selected wavelength as a function of time in at least two time windows wherein said system further comprises a data processing unit with software for correcting an emission light signal measured within a first time window within the time window defined by an excitation light pulse with an emission light signal measured within a second time window to follow the first time window not at all overlapping with said time window defined by the excitation pulse.

9. A software product for a system for carrying out the method according to claim 1, wherein the software product is embodied in a computer readable medium and wherein said software product, in combination with a data processing unit, is capable of correcting an emission light signal measured within a first time window within the time window defined by an excitation light pulse with an emission light signal measured within a second time window to follow the first time window not at all overlapping with said time window defined by the excitation pulse.

* * * * *